(12) United States Patent
Troyer et al.

(10) Patent No.: US 6,506,412 B2
(45) Date of Patent: Jan. 14, 2003

(54) TREATMENT OF DRY EYE SYNDROME

(75) Inventors: Ellen M. Troyer, Sausalito, CA (US); Spencer P. Thornton, Nashville, TN (US); K. Steven Whiting, San Diego, CA (US); Richard Kaufman, Marina Del Rey, CA (US)

(73) Assignee: ScienceBased Health, Carson City, NV (US)

( * ) Notice: Subject to any disclaimer, the term of this patent is extended or adjusted under 35 U.S.C. 154(b) by 0 days.

(21) Appl. No.: 09/725,608

(22) Filed: Nov. 29, 2000

(65) Prior Publication Data

US 2002/0099100 A1 Jul. 25, 2002

(Under 37 CFR 1.47)

(51) Int. Cl.[7] .................. A61K 35/60; A61K 33/06; A61K 31/355; A61K 31/07

(52) U.S. Cl. .................. 424/523; 424/682; 424/697; 514/558; 514/912; 514/915; 514/725

(58) Field of Search .................. 424/523, 682, 424/697; 514/558, 912, 915, 725

(56) References Cited

U.S. PATENT DOCUMENTS

| | | | |
|---|---|---|---|
| 3,993,775 A | | 11/1976 | Williams |
| 4,388,324 A | | 6/1983 | Horrobin |
| RE31,836 E | | 2/1985 | Horrobin |
| 4,977,187 A | | 12/1990 | Horrobin |
| 5,032,392 A | * | 7/1991 | Varma |
| 5,120,760 A | * | 6/1992 | Horrobin |
| 5,328,691 A | * | 7/1994 | Horrobin et al. |
| 5,496,558 A | * | 3/1996 | Napolitano et al. |
| 5,677,335 A | | 10/1997 | Robertson |
| 5,886,054 A | * | 3/1999 | Van Nieuw Amerongen et al. |
| 6,060,486 A | | 5/2000 | Urashima |
| 6,107,334 A | * | 8/2000 | Chilton |
| 6,245,811 B1 | * | 6/2001 | Horrobin et al. |
| 6,248,368 B1 | * | 6/2001 | Valletta |
| 6,284,268 B1 | * | 9/2001 | Mishra et al. |

OTHER PUBLICATIONS

Horrobin D.F., Campbell A., McEweh C.G., Treatment of the Sicca Syndrome, etc., 1981:20:253–4, *Prog. Lipid Research*.

Oxholm P., Manthorpe R., Prause J.U., Horrobin D.F., Patients w/Primary Sjogren's, etc., 1986:15(2):103–8, *Scand. J. Rheumatology*.

\* cited by examiner

*Primary Examiner*—Christopher R. Tate
(74) *Attorney, Agent, or Firm*—Thomas M. Freiburger

(57) ABSTRACT

Dry-eye syndrome and other dryness effects of glandular malfunction are treated orally by a combination which includes a source of omega-3 fatty acid, a source of omega-6 fatty acid, vitamin A, vitamin B6, a source of magnesium and a water-soluble antioxidant. The preparation preferably is contained in a capsule. In a preferred form of the preparation and of the method, the preparation also includes mucin and cold water fish oil. The fatty acids preferably are contained in blackcurrant seed oil, and the water-soluble antioxidant is preferably in the form of vitamin C.

20 Claims, No Drawings

TREATMENT OF DRY EYE SYNDROME

BACKGROUND OF THE INVENTION

This invention concerns generally the treatment of disease, and more particularly the treatment of human glandular function disorders involving oil and mucus secreting glands and/or tear secreting (lacrimal) glands leading to dryness in the eyes, mouth or other areas.

Dry-eye syndrome is a common condition affecting approximately one in five Americans. It is characterized by symptoms including dry, irritated eyes, excessively watery eyes, burning and stinging, a foreign body sensation, and blurred vision. Despite the diverse causes of dry eye syndrome, in all dry eye conditions the ocular surface epithelium undergoes squamous metaplasia, manifested by loss of goblet cells, mucin deficiency and keratinization. These changes result in tear film instability, which leads to the clinical symptoms of dry eye syndrome.

Human tears are produced by the lacrimal glands. Tears are distributed by blinking, undergo evaporation from the ocular surface, and drain through the nasal lacrimal duct. An abnormality in any of these processes can cause dry eye. For example, Sjogren's Syndrome is caused by damage to the lacrimal gland, which disables the reflex aqueous tear production process. Meibomian gland dysfunction, or MGD, alters the oily layer in tears, causing increased evaporation. The tears comprise three layers, only one of which is the aqueous saline layer. A layer of mucin, a slimy substance produced by the goblet cells, coats the corneal epithelium. The aqueous tear layer, produced by the lacrimal gland and approximately 0.9% saline, floats on the mucin layer. Outside the aqueous tear layer is an oil layer which protects the tears, this oil being produced by glands located in the eyelid. This oil is actually an aqueous-lipid mixture, a thin, fine film which floats on top of the tears and limits evaporation.

Essential fatty acids (EFAs) are critical to optimum ocular functioning. EFAs cannot be synthesized by the human body and thus must be obtained from the diet. The omega-6 essential fatty acid, linoleic acid, is of particular importance to dry eye syndrome. The body converts linoleic acid into prostaglandin E1 (PGE1) in the following step-wise sequence: linoleic acid, gamma-linolenic acid (GLA), dihomo-gamma-linolenic acid, prostaglandin E1. It is important that omega-3 fatty acids be in balance with the omega-6 fatty acids.

Enzymatic conversion of linoleic acid to PGE1 may be impaired by a wide variety of factors, including an insufficiency or imbalance of fatty acid precursors; a deficiency of nutrient conversion factors; aging; viral infections; consumption of foods rich in trans-fatty acids and saturated fats; and alcohol. Thus, a direct source of GLA must be provided in many circumstances in order to form prostaglandin E1 for proper tear production.

Horrobin and others have suggested that an effective approach to the treatment of dry eye disorders may be to address the biochemical basis of an intact tear film. See Horrobin D. F., Campbell A., McEwen C. G.: Treatment of the Sicca Syndrome and the Sjogren's Syndrome with E.F.A., Pyroxidine and Vitamin C. Prog Lipid Res 8(4): 253–4, 1981; and Oxholm, P., Manthorpe R., Prause J. U., Horrobin D.: Patients with Primary Sjogrn's Syndrome Treated for 2 Months With Evening Primrose Oil. Scand J Rheumatology 1986: 103–108. In this work the authors evaluated the use of supplemental intake of the essential fatty acids, linoleic and gamma-linolenic acids, vitamin B6, and vitamin C to treat dry eye. These nutrients are necessary components of the pathway for biosynthesis of PGE1, which is necessary for aqueous tear secretion by the lacrimal gland. See also Horrobin Patents U.S. Pat. Nos. 4,388,324 and Re31,386, and U.S. Pat. Nos. 3,993,775, 4,977,187, 5,677, 335 and 6,060,486.

However, the work of Horrobin et al., while it may have been effective to increase aqueous tear secretion via the lacrimal gland, did not address all issues regarding dry eye syndrome. In many patients with dry eye syndrome, the function of the lacrimal glands is normal, with adequate aqueous tear production; it is one of the other tear layers described above which is inadequate. Enhancement of the function of these other glands, or supplying the deficiencies exhibited by the glands, was not adequately addressed in the prior studies.

Most previous treatments for dry eye syndrome have involved the topical application of eye drops, which can be required very frequently in some patients. However, in addition to the Horrobin patents referenced above, Urashima U.S. Pat. No. 6,060,486 and Robertson U.S. Pat. No. 5,677, 335 (listed above) are directed to oral approaches to the treatment of dry eye syndrome.

SUMMARY OF THE INVENTION

The treatment embodied in the present invention addresses all of the underlying cellular factors that may produce dry eye syndrome (or other glandular-related dryness), including deficiency of omega-3 EFAs and prostaglandin E1 (PGE1), ocular deficiency of vitamin A, and abnormal levels of mucus, glycoproteins produced by conjunctival goblet cells. The orally-administered preparation comprises a unique combination of biologically active ingredients. The preparation does not merely treat symptoms of dry eye, as do prior topical lubricating products or hypotonic solutions and mucolytic agents that can decrease symptoms of excess mucin strands, or other additives that can help lower tension at the water-oil interfaces and mimic some actions of mucin network. The treatment according to the invention addresses the underlying causes of dry eye syndrome, rather than providing temporary palliative measures. The invention addresses the biochemical basis of an intact tear film, treating the causative factors of dry eye syndrome and supporting the body's natural tear formation.

In one preferred embodiment of the preparation and treatment according to the invention, the preparation includes blackcurrant seed oil, as a source of both omega-3 and omega-6 fatty acids; pyridoxal 5-phosphate, the active form of vitamin B6; ascorbic acid and ascorbil palmitate (vitamin C); vitamin A; mucin; and magnesium, preferably in the form of magnesium sulfate. The preparation preferably also includes cod liver oil, as an additional source of omega-3 essential fatty acids.

One important aspect of the formulation of the invention, for effective treatment, is the provision of the omega-3 fatty acids from both plant and fish sources, due to the synergistic combination of the two types of fatty acids from these difference sources.

These and other objects, advantages and features of the invention will be apparent from the following description of a preferred embodiments.

DESCRIPTION OF PREFERRED EMBODIMENTS

In a preferred embodiment of a preparation for treating dry eye syndrome, and also for treating dryness in the mouth, female vaginal dryness or other glandular-related dryness, the preparation of the invention includes the following components:

| | |
|---|---|
| Vitamin A (from retinyl palmitate) | 1040 IU (or a range of about 200 to 5000 IU) |
| Vitamin C (from calcium ascorbate) | 90 mg (or at least about 50 mg) |
| Vitamin B6 (from pyridoxal 5-phosphate) | 6.3 mg (or a range of about 2.0 to 20 mg) |
| Magnesium (from magnesium sulfate) | 20 mg (or a range of about 10 to 50 mg) |
| Black Currant Seed Oil (or other plant source providing gamma linolenic acid (GLA)) | 750 mg (or at least about 300 mg) |
| Mucin | 150 mg (or a range of about 100 to 300 mg) |
| Cod Liver Oil (or other cold water fish oil) | 1.6 mg (or a range of about 0.5 to 3.0 mg) |

This preparation preferably is administered to a patient twice daily, advantageously taken with meals (it should be understood that the word "preparation" or "formulation" as used herein is intended to refer collectively to these substances and amounts whether taken separately by a patient or whether included in a single capsule or other ingestible medium).

The above is a preferred form of the treatment of the invention, but variations are possible. The above formulation addresses not only the adequate production of aqueous tears, the middle layer of a healthy tear film on the eye, but also the slippery substances which comprise the inner layer directly coating the epithelium and the outer oily layer over the aqueous tear layer, which helps prevent evaporation. The ranges indicated for the carious components are probable approximate limits as projected from research and the applicants' knowledge of the functional role played by each substance.

The following is a discussion of the components of the above formulation.

Black Currant Seed Oil

Black currant seed oil contains both omega-3 and omega-6 fatty acids, as well as gamma-linolenic acid (GLA). These EFAs regulate membrane fluidity and membrane function, serve as precursors to eicosanoids (prostaglandins, thromboxanes, and leukotrienes), exhibit enzyme-like activities, and serve as substrates for enzymes, helping to prevent the drying and atrophy of tear glands. Research finds statistically significant improvement in overall ocular scores in patients with Sjogren's syndrome treated with linoleic acid and gamma-linolenic acid (GLA) over control groups. Omega-3 fatty acid, omega-6 fatty acid and GLA together make up about 31% of black currant seed oil. Thus, the preferred formulation contains at least about 94 mg of these three components together, and preferably contains about 235 mg of these.

Omega-3 Fatty Acid

Omega-3 fatty acid is an "essential" fatty acid, required in amounts of about 500 mg daily. Commercially it is derived from fish oil, microalgae, and certain plant foods such as flax seed, borage, evening primrose and currant oils.

Omega-3 and omega-6 fatty acids are both essential, but omega 3s are more depleted in American diets and therefore more important in nutritional supplements. Dietary omega-3 EFAs come from both animal and plant sources. The major source of the particular omega-3 fatty acid DHA (docosahexaeonic acid) is cold water fish such as salmon, tuna, cod, mackerel, sardines and trout. Omega-3s are also found in walnuts, canola oil, flaxseed and green leafy vegetables.

Omega-3s reduce formation of the hormonelike prostaglandins which trigger inflammatory processes. They do this by replacing excessive omega-6 fatty acids, which readily oxidize into free radicals. In most Americans the omega-6s overwhelm and dominate activity in cells, and omega-3s help restore the balance. Animal studies have shown that omega-3 fatty acids increase antioxidant enzyme activity and omega-6 oils reduce it. Omega-6s are essential, but they must be in balance with omega-3s (similarly to the needed balance between HDL and LDL in the blood).

Pyridoxal 5-Phosphate (Vitamin B6)

Pyridoxal 5-phosphate is the active form of vitamin B6. It is necessary for the normal activity of the enzyme delta-6-desaturase, which converts cis-linoleic acid to GLA, and GLA into the precursor of PGE1, dihomo-gamma-linolenic acid. Vitamin B6, or pyridoxal 5-phosphate, is thus a micronutrient cofactor supporting and enhancing conversion of linoleic acid to gamma linolenic acid (GLA). Research using pyridoxal 5-phosphate in combination with essential fatty acids and vitamin C has demonstrated improvement within two to six weeks in two thirds of treated subjects.

Ascorbic Acid (Vitamin C) and Ascorbyl Palmitate

Vitamin C is required for the conversion of dihomo-gamma-linolenic acid into prostaglandin E1, and thus is critical for tear production. Ascorbic acid in tears serves as anti-flammatory role in the eye's defense system. Vitamin C could be replaced by another water-soluble antioxidant, but vitamin C is preferred.

Vitamin A

Vitamin A regulates the proliferation and differentiation of corneal epithelial cells and preserves conjunctival goblet cells. It is required for the synthesis of mucin glyco-proteins in the eye. A deficiency of vitamin A can result in abnormal epithelial cells in the eyelids, lacrimal glands, and conjunctiva. Vitamin A deficiency can also produce abnormalities of the precorneal tear film and tear glands, and induce the occurrence of dry eye syndrome. Vitamin A treatment has been shown to reverse many of the underlying cellular changes that lead to dry eye syndrome.

Mucin

The pre-ocular tear film is a complex biochemical fluid produced by the lacrimal glands and epithelial cells on the ocular surface. The symptoms of dry eye syndrome may result from deficiencies and disturbances of the mucin network. For example, aqueous tear deficiencies lead to the ocular surface disorder, keratoconjunctivitis sicca (Sicca), a dry eye syndrome. Sicca results from abnormal terminal differentiation of the ocular surface epithelium and is associated with a marked reduction in mucin production by the goblet cells. The inclusion of mucin in the preferred form of the preparation is to directly supply mucin glycoproteins for the maintenance of the mucin network layer in the tear film. The mucin preferably is from an animal source.

Magnesium

Magnesium is another essential micronutrient cofactor in the conversion of linoleic acid into GLA.

Cod Liver Oil

Cod liver oil is an additional source of essential fatty acids, specifically omega-3 fatty acid. Other cold water fish oils can be used, but cod liver oil is concentrated. As noted above, the cold water fish oil provides the important omega-3 fatty acid DHA.

The following examples illustrate the effectiveness of the preparation outlined above, in the preferred formulation:

EXAMPLE 1

B.T., female, age 32 presented with history of red, dry, itchy eyes following yard work, felt to be due to exposure to allergens while working in yard. Diagnosis: allergic conjunctivitis with squamous metaplasia.

Treatment: a preparation in the preferred form as described above, taken internally twice daily with meals.

Four week evaluation: Much improved corneal surface with greater tear film stability and reduced conjunctival injection.

EXAMPLE 2

M.G., female, age 28 reported dry eyes around the time of her monthly periods, in addition to vague urinary complaints (burning, frequency). Diagnosis: hormonal imbalance with corneal squamous metaplasia and mucin deficiency in addition to gynecologic symptoms.

Treatment: the preferred form preparation as described above, taken internally twice daily with meals.

Two week and six week evaluation: improvement of both ocular and gynecologic symptoms.

EXAMPLE 3

F.R., male, age 36, with history of long-term contact lens wear. Eyes felt dry, itchy, made worse with contact lens wear. Diagnosis: Inadequate ocular nutrition with recurrent erosion and keratinization.

Treatment: the preferred form preparation as described above, taken internally twice daily with meals.

Four week evaluation: Marked improvement of corneal surface lubrication, reduced keratinization and no sign of recurrent erosion.

EXAMPLE 4

J.M., female, age 38. Immediate post-op Lasik. Reported dry, itchy eyes with visual blurring. Diagnosis: Neurovascular insufficiency with interruption of interstitial fluid circulation.

Treatment: a preparation in the preferred form as described above, taken internally twice daily with meals.

Two and four week evaluation: Relief within 36 hours of dry itchy eyes. Blurring relieved after one week. Slit lamp biomicroscopy normal at two week evaluation.

EXAMPLE 5

S.W., male, age 57, post-cataract surgery with implantation of SI 41 IOL (Multifocal IOL). Eyes dry, vision blurred with additional haloing and blur. Diagnosis: Stromal microedema with squamous metaplasia and mucin deficiency.

Treatment: a preparation as described above, taken internally twice daily with meals.

Two and four week valuation: Blur markedly diminished. Dryness much reduced. Halos still present but not as marked. Slit lamp biomicroscopy reveals essentially normal corneal appearance with minimal metaplasia.

EXAMPLE 6

An ophthalmologist who is a foremost authority and world-renowned surgeon in array implants, in which the natural accommodating lens of the eye is replaced by a multi-focal length lens array (multifocal IOL), underwent the procedure himself and had the natural lenses of both eyes replaced by inter-ocular array implants. After surgery, as is typical, the distant vision was good, but the near vision was initially somewhat blurred and required several months to improve to full sharpness. Approximately one and one half years after the surgery, the ophthalmologist's left eye exhibited some problems of distorted vision. This seemed to indicate the need for a further laser surgical procedure that is required in approximately 10% to 50% of post-operative patients receiving the multifocal IOL. However, the ophthalmologist put himself on the treatment as described above, using the preferred form of preparation and taking the same dosage twice daily with meals. Within two weeks, improvement was noted in the left eye. After one full month of the treatment, the symptoms of distorted vision had fully disappeared. After this full improvement, the ophthalmologist wanted to confirm the effect was from the treatment and thus discontinued taking the preparation. Within three to four days, the ophthalmologist's vision again deteriorated, to the same condition experienced previously. A week later, the treatment was resumed and the symptoms again disappeared. Moreover, the ophthalmologist had a patient who underwent the same implantation of the multifocal IOL, and the patient experienced the same effect. Much after the surgery, the patient experienced distorted vision similar to that of the ophthalmologist. The ophthalmologist suggested the treatment using the preparation in its preferred form as described above, taken twice daily with meals. After a period of time similar to that experienced by the ophthalmologist, the patient's vision markedly improved, and the distorted vision was corrected. After a further period during which the patient was on this treatment, the patient's supply of the preparation was depleted, and the patient went several days without the treatment. He noticed the symptoms of distorted vision returning, obtained an additional supply of the preparation and resumed treatment, and the symptoms again disappeared and did not reappear as long as the treatment was continued. The ophthalmologist observed that the major controlling factor in how well a patient can focus at different distances using the multi-focal lens of an inter-ocular implant, is how well the patient's cornea is functioning. The use of the preparation described above helps assure that the cornea is functioning at peak and optimal performance, and this supports the function of the array implant in all of its focal zones.

Patients taking the above preparation for a period of at least several weeks have additionally reported increased salivary secretion, vaginal secretion and joint mobility.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

We claim:

1. A method for treating insufficient glandular production of lubricating liquids in an individual, comprising:
   administering orally to a patient a preparation including effective amounts of:
   omega-3 fatty acid,
   omega-6 fatty acid,
   vitamin A, in an amount effective to support synthesis of mucin glyco-proteins,
   one or more micronutrient cofactors in an amount effective to support and enhance conversion of linoleic acid to gamma-linolenic acid, said one or more micronutrient cofactors being selected from the group consisting of magnesium and vitamin B6,
   a water-soluble antioxidant, and mucin.

2. The method of claim 1, wherein the water-soluble antioxidant comprises ascorbic acid.

3. The method of claim 1, wherein the sources of omega-3 fatty acid and omega-6 fatty acid comprises blackcurrent seed oil.

4. The method of claim 3, wherein the preparation further includes cold water fish oil as a source of omega-3 fatty acid.

5. The method of claim 1, wherein the preparation further includes cold water fish oil as a source of omega-3 fatty acid.

6. The method of claim 1, wherein the micronutrient cofactors include both vitamin B6 and magnesium.

7. The method of claim 1, as a treatment for dry eye syndrome.

8. The method of claim 1, as a treatment for surgically-induced dry eye syndrome.

9. A method for treating insufficient glandular production of lubricating liquids in an individual, comprising:
 administering orally to a patient a preparation including effective amounts of:
  omega-3 fatty acid, omega-6 fatty acid, and GLA in a combined amount of at least about 94 mg,
  vitamin A, at least about 1000 iu,
  micronutrient cofactors effective to support and enhance conversion of linoleic acid to gamma-linolenic acid, including at least about 6 mg of vitamin B6 and at least about 20 mg magnesium as magnesium sulfate, and
  a water-soluble antioxidant.

10. The method of claim 9, wherein the water-soluble antioxidant is vitamin C, present in at least about 50 mg.

11. The method of claim 9, wherein the preparation further includes mucin, present in at least about 100 mg.

12. The method of claim 11, wherein the preparation further includes cold water fish oil, present in at least about 0.5 mg, as a source of omega-3 fatty acid.

13. The method of claim 9, wherein the preparation includes blackcurrant seed oil as a source of both omega-3 and omega-6 fatty acids, the seed oil being present in at least about 300 mg.

14. A method for treating insufficient glandular production of lubricating liquids in an individual, comprising:
 administering orally to a patient a preparation including effective amounts of:
  (a) omega-3 fatty acid, omega-6 fatty acid, and GLA, a combined total of about 235 mg;
  (b) vitamin A, at least about 1040 iu,
  (c) vitamin C as a water-soluble antioxidant, about 90 mg;
  (d) vitamin B6 as a micronutrient cofactor effective to support and enhance conversion of linoleic acid to gamma-linolenic acid, about 6.3 mg; and
  (e) magnesium as magnesium sulfate as a micronutrient cofactor effective to support and enhance conversion of linoleic acid to gamma-linolenic acid, about 20 mg.

15. The method of claim 14, wherein the preparation further includes mucin, at least about 100 mg.

16. The method of claim 14, wherein the preparation further includes at least about 1.6 mg cold water fish oil.

17. A method for treating insufficient glandular production of lubricating liquids in an individual, comprising:
 administering orally to a patient a preparation including effective amounts of:
  omega-3 fatty acid, omega-6 fatty acid and GLA in a combined amount of at least about 94 mg,
  vitamin A, in a range of about 200 to 5000 iu,
  micronutrient cofactors effective to support and enhance conversion of linoleic acid to gamma-linolenic acid, including vitamin B6 in a range of about 2 to 20 mg and magnesium in a range of about 10 to 50 mg,
  a water-soluble antioxidant, and
  mucin, in a range of about 100 to 300 mg.

18. The method of claim 17, wherein the water-soluble antioxidant comprises ascorbic acid, at least about 50 mg.

19. The method of claim 18, including blackcurrent seed oil as a source of omega-3 fatty acid and omega-6 fatty acid.

20. The method of claim 19, wherein the preparation further includes cold water fish oil as a source of omega-3 fatty acid.

* * * * *